(12) United States Patent
Lu

(10) Patent No.: US 7,727,560 B2
(45) Date of Patent: Jun. 1, 2010

(54) TREATING CANCER, LIVER, KIDNEY, PLATELET AND HEMOPOIETIC DISORDER OR COMPLICATION

(76) Inventor: Sou Yi Lu, 4th Floor, No. 51 DaDong Street, Banchiao, Taipei Hsein (TW) 220

( * ) Notice: Subject to any disclaimer, the term of this patent is extended or adjusted under 35 U.S.C. 154(b) by 0 days.

(21) Appl. No.: 10/847,546

(22) Filed: May 18, 2004

(65) Prior Publication Data

US 2005/0260288 A1      Nov. 24, 2005

(51) Int. Cl.
*A61K 36/00* (2006.01)
(52) U.S. Cl. .................................................. 424/725
(58) Field of Classification Search ................ None
See application file for complete search history.

(56) References Cited

U.S. PATENT DOCUMENTS

| 4,636,463 | A | * | 1/1987 | Altman et al. | 435/7.92 |
|---|---|---|---|---|---|
| 4,985,543 | A | * | 1/1991 | Sugita et al. | 530/396 |
| 5,830,887 | A | * | 11/1998 | Kelly | 514/182 |
| 6,004,558 | A | * | 12/1999 | Thurn et al. | 424/757 |
| 6,129,919 | A | * | 10/2000 | Chen et al. | 424/195.15 |
| 6,562,380 | B1 | * | 5/2003 | Kelly | 424/757 |
| 6,669,956 | B2 | * | 12/2003 | He et al. | 424/464 |
| 2002/0160060 | A1 | * | 10/2002 | Kim Chen et al. | 424/757 |

FOREIGN PATENT DOCUMENTS

JP           2001089346        *   4/2001

OTHER PUBLICATIONS

Broder, G. Presentation Highlights—Complications of Cancer. 3rd Annual Joint Cancer Conf. Florida Univ. Jan. 1999. 9 pages, Downloaded from Internet site www.moffitt.usf.edu.*
Wecksler et al. Acta Cientifica Venezolana. 1968. vol. 9, No. 4, pp. 154-156, CAPLUS Abstract enclosed.*
Swaffar et al. Anti-Cancer Drugs. 1995. vol. 6, No. 4, pp. 586-593, EMBASE Abstract enclosed.*
Markman, M. Cleveland Clinic J. Med. 1994. vol. 64, No. 2, pp. 105-114.*
Ellis et al. Am. J. Clin. Oncol. 1986. vol. 9, No. 6, pp. 533-536, MEDLINE Abstract enclosed.*
Tartter et al. Am. J. Surgery. 1986. vol. 152, No. 5, pp. 479-482, MEDLINE Abstract enclosed.*
Feld, R. Lung Cancer. 1994. vol. 10, Suppl. 1, pp. S307-S317, MEDLINE Abstract enclosed.*
L.W. Lee, Study on Anticancer Activity by Orally Administered ConA; J. Chinese Oncol. Soc. II(3), 27-34. 1995. Taipei. Taiwan.
H. Louis, Production and Role of IL-10 in ConA Induced-Hepatitis; J. Hepatology, 1997. USA.
Y. Kaneko, Augmentation of $V\alpha 14NKT$ Cell-Mediated Cytotoxicity by IL-4 in an Autocrine Mechanism Resulting in Development of ConA Induced Hepatitis; J. of Experimental Medicine vol. 191. No. 1, Jan. 3, 2000; USA.
Egan, H.S., Supression of a Thymus Dependent Humoral Reponse in Mice by ConA In Vivo.; Cell Immunol; vol./issue 18:1. 1975. Chicago. USA.
International Immunology, vol. 11, No. 9. 1491-1500, Sep. 1999 Immunopathogenesis of hepatic fibrosis in chronic liver injury induced by repeatedly administered concanava.
Biochem J. Nov. 15, 2001: 360(Pt 1): 217-224. Copyright notice Canatoxin, a toxic protein from jack beans (*Canavalia ensiformis*), is a variant form of urease (EC 3.5.1.5.

* cited by examiner

*Primary Examiner*—Christopher R. Tate

(57) ABSTRACT

The present invention relates to a method of suppressing malignant conditions, including cancer with complications such like hepatitis and platelet disorder in bleeding, by administering a composition of an extract of *Canavalia ensiformis*. Also, the invention is nontoxic to the individual and for improving functions of kidney as well as of liver, especially when involved in cancer.

5 Claims, 7 Drawing Sheets

TREATING CANCER, LIVER, KIDNEY, PLATELET AND HEMOPOIETIC DISORDER OR COMPLICATION

BACKGROUND OF THE INVENTION

This invention concerns treating one or more disorders or complications in a subject having cancer, whereby the disorder or complication is hepatitis, hemopoietic disorder, platelet disorder, and/or renal disease.

Most chemotherapy for cancer patients will cause greatly damage to important organs so called side effects, which usually include such as hepatitis, hemopoietic deficiency or renal disorders.

Therefore, valid methods for improving functions of organs or in cancer therapy were developed to use a *Canavalia ensiformis* extract for that purpose effectively.

In the past, a purification of *Canavalia ensiformis*, concanavalinA (ConA) had been tried in vivo and in vitro. Pure ConA was reported to induce toxic effects such as hepatitis and hemagglutination in vivo. However, neither ConA nor *Canavalia ensiformis* was proved in vivo to against cancer or complication. This invention was by using a *Canavalia ensiformis* extract, not a pure ConA, as an alternative to suppress cancer as well as other disorders.

BRIEF SUMMARY OF THE INVENTION

Accordingly, it is an object of this invention to provide an effective method of suppressing disorders.

Another object of this invention is to provide an effective method of suppressing cancer.

Another object of this invention is to provide an effective method of improving functions of organs.

Another object of this invention is to provide a composition of *Canavalia ensiformis* extract for effects of tumor cytotoxicity.

Other and further objects of this invention will become apparent from the illustrative embodiments, and various advantages not referred to herein will occur to one skilled in the art on employment of the invention in practice.

DETAILED DESCRIPTION OF THE INVENTION

Figure 1:
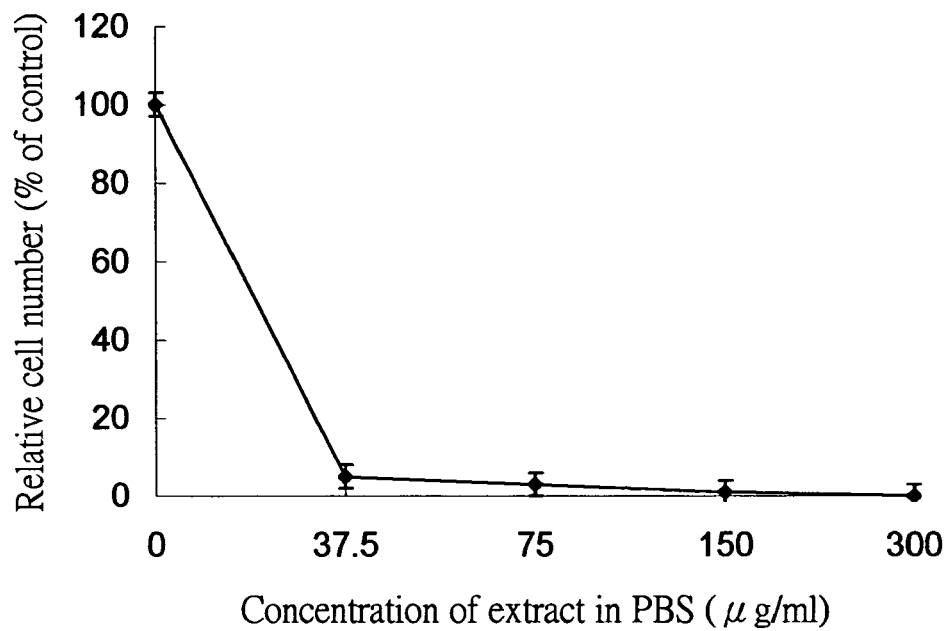
FIG. 1 shows a MCF-7 cell proliferation assay in which the ordinate indicates relative cell number (% of control), and the abscissa indicating the concentration of extract in solution (mg/ml); $IC_{50}$: 24.3 µg/ml

The inventor has been investigating in finding an effective method for suppressing cancer, malignant complications, hepatitis or platelet disorder. Some extracts of herbs maybe possibly useful for cancer therapy, such as *Canavalia ensiformis* extract of its roots, seeds, flowers, leaves or branches. The preferred embodiment proved a *Canavalia ensiformis* extract plays an excellent role not only in suppressing malignant complication including cancer, hepatitis, renal disorder and platelet disorder but also in improving functions of liver and kidney. A preferred embodiment of process for preparing the *Canavalia ensiformis* extract may be by salting the ground seeds of *Canavalia ensiformis* in Nacl solution, $(NH4)_2SO_4$ extracting, water extracting and spray drying. The powder of *Canavalia ensiformis* extract (herein referred to as "extract") would be then obtained. It may be as a powder drug itself or dissolved in aqueous solvent and used as a pharmaceutical solution.

There is no particular restriction for the administration form. The formulations for oral administration illustratively include tablets, pills, granules, soft and hard capsules, dispersions, fine granules, powders, emulsions, suspensions, syrups, elixirs and the like.

For the formulation of the effective ingredient of this present invention, routine processes should be followed, employing appropriately surfactants, excipients, coloring agents, flavorings, sweetening agents, preservatives, stabilizers, buffers, suspending agent, isotonic agents, vitamins, minerals, nutritional supplements and other substances.

The content of the "extract" should be dosed appropriately, depending on the extent of the condition of the patient administration form, the age and the like.

Generally, the recommended dosage is within 2 g/kg, that is 2 grams of the "extract" of per kilogram of bodyweight as a composition for oral administration.

This invention should be understood more readily with reference to the following examples; however these examples are intended to illustrate the invention and are not to be constructed to limit the scope of the invention.

BEST MODE OF CARRYING OUT THE INVENTION

Example 1

The ground seeds of *Canavalia ensiformis* as crude powdered form were salted into more than 30% of sodium chloride solution and stirred continuously for approximately 4 hours then precipitation. Collecting the precipitate and dissolving again to obtain the suspension, then $(NH4)_2SO_4$ added for the precipitate collect, then dissolving it in water for 4 hours for precipitation.

The precipitate was removed out to obtain a soluble extract and the same was spray dried to result in a powder of *Canavalia ensiformis* extract.

To prove the medical effect of this invention, a plurality of experiments were performed as follows.

Dissolved the "extract" in aqueous solvent, PBS (phosphate buffer solution), to an original concentration at 1 mg of "extract"/1 ml of PBS and be ready to use.

In Vitro Test of Tumor Cytotoxicity:

All the following cell lines are from ATCC, USA, except the TSGH8301.

(10) MCF-7, cells of mammary gland of human breast adenocarcinoma.

(11) LLC-1, cells of Lewis lung carcinoma.

(12) SW480, cells of a primary adenocarcinoma of the human colon.

(13) PC-3, cells of metastatic site of human prostate carcinoma.

(14) TSGH 8301, cells of human bladder carcinoma.

(15) Hela, epithelia cells of human cervical adenocarcinoma.

(16) Paca-2, cells of human pancreas carcinoma.

(17) AGS, cells of human garstric adenocarcinoma.

(18) Hepa G2, cells of human hepatocellular adenocarcinoma.

The original concentration at 1 mg of extract/1 ml of PBS (ie, 1 mg/ml) was separately diluted into 4 tubes of concentration at 300 μg/ml, 150 μg/ml, 75 μg/ml and 37.5 μm/ml.

Example 2

The MCF-7 cells were added as the number of $1 \times 10^4$ cells/ml to wells of 96-well plate. Each well was added therein above different concentration of the "extract" solution, i.e, 300 μg/ml, 150 μg/ml, 75 μg/ml and 37.5 μg/ml respectively for incubation of the cancer cells for 72 hours.

Then added 0.1 ml of culture medium and 0.1 ml of M.T.T for 2 hours, incubated with extracting solution for 2 hours and obtained data by ELISA reader as shown in FIG. I.

It proved the "extract" was cytotoxic to MCF-7 and other above mentioned cancer cells with apparent medical effect in following experiments of the invention.

Example 3

Figure 2:
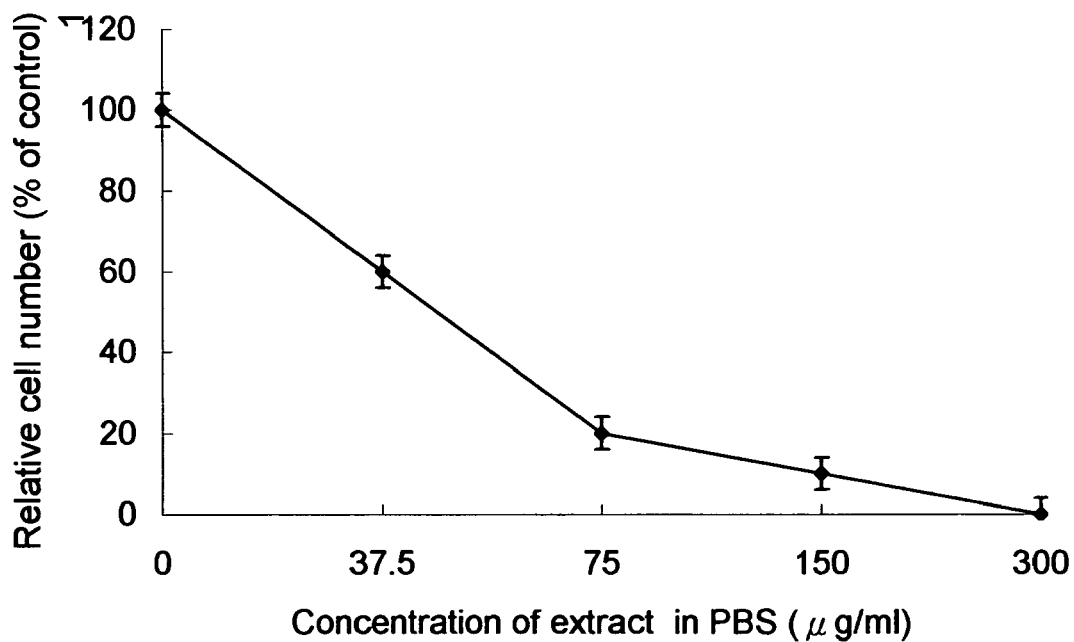
FIG. 2 shows a LLC-1 cell proliferation assay in which the ordinate indicates relative cell number (% of control), and the abscissa indicating the concentration of extract in solution (mg/ml); $IC_{50}$: 49.2 µg/ml

The experimental procedures of Example 2 are repeated by investigating the cells of LLC-1 to obtain data as results shown in FIG. 2.

Example 4

Figure 3:
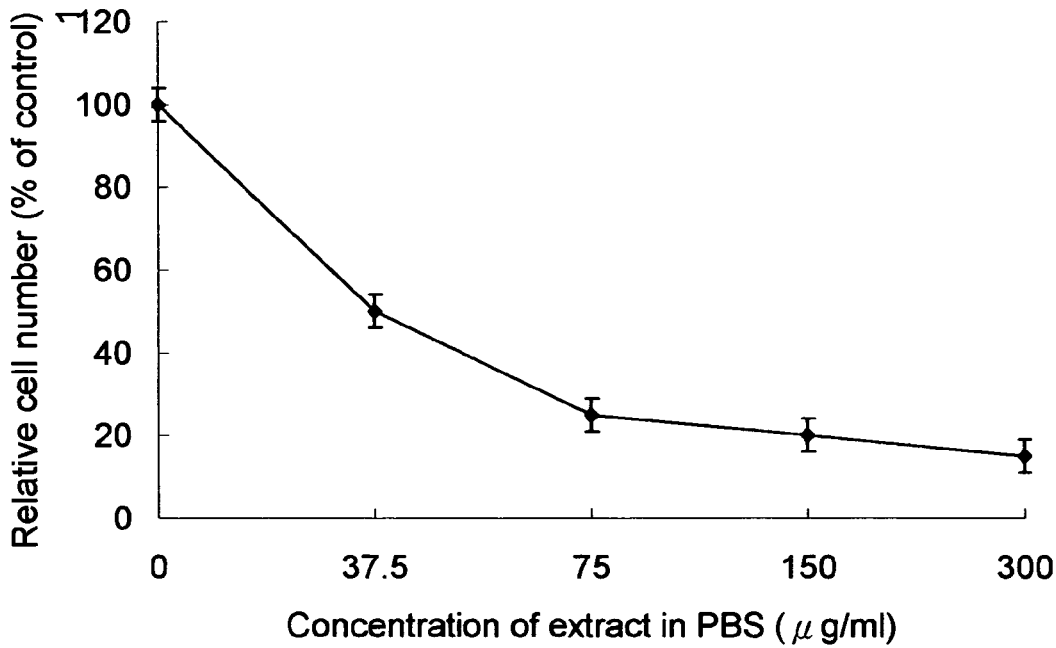
FIG. 3 shows a SW480 cell proliferation assay in which the ordinate indicates relative cell number (% of control), and the abscissa indicating the concentration of extract in solution (mg/ml); $IC_{50}$: 36.5 µg/ml

The experimental procedures of Example 2 are repeated by investigating the cells of SW480 to obtain data as results shown in FIG. 3.

Example 5

Figure 4:
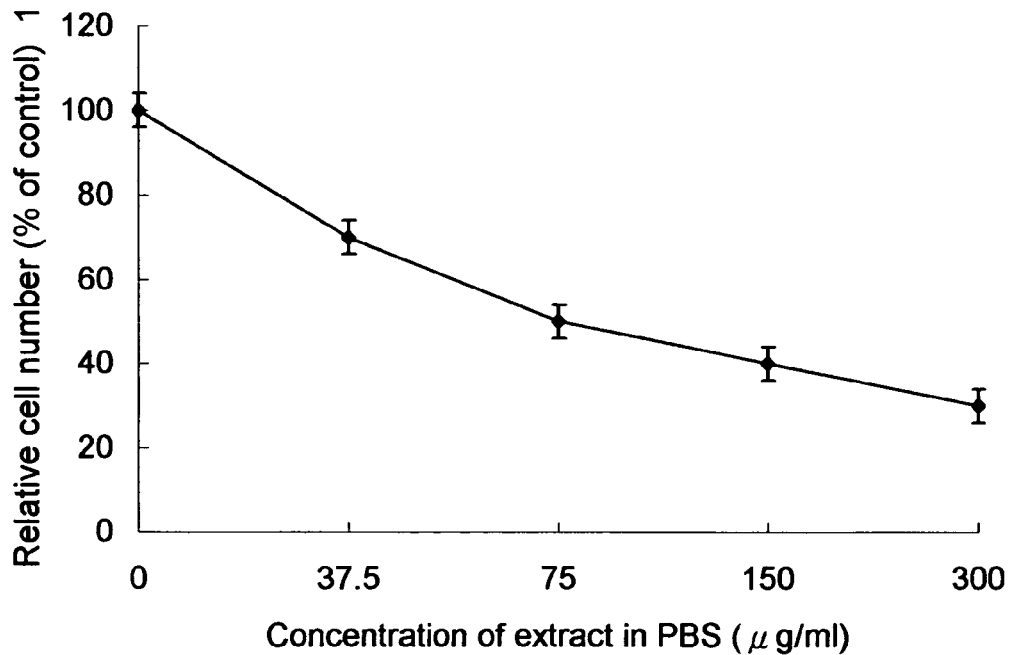
FIG. 4 shows a PC-3 cell proliferation assay in which the ordinate indicates relative cell number (% of control), and the abscissa indicating the concentration of extract in solution (mg/ml); $IC_{50}$: 74.5 µg/ml

The experimental procedures of Example 2 are repeated by investigating the cells of PC-3 to obtain data as results shown in FIG. 4.

Example 6

Figure 5:
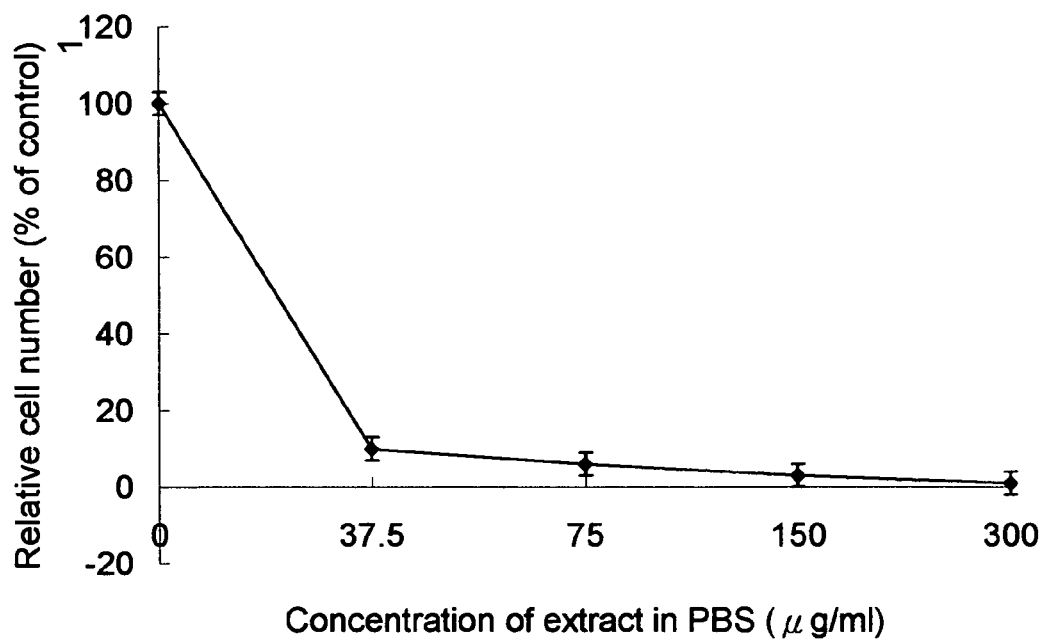
FIG. 5 shows a TSGH8301 cell proliferation assay in which the ordinate indicates relative cell number (% of control), and the abscissa indicating the concentration of extract in solution (mg/ml); $IC_{50}$: 31.8 µg/ml

The experimental procedures of Example 2 are repeated by investigating the cells of TSGH8301 to obtain data as results shown in FIG. 5.

Example 7

Figure 6:
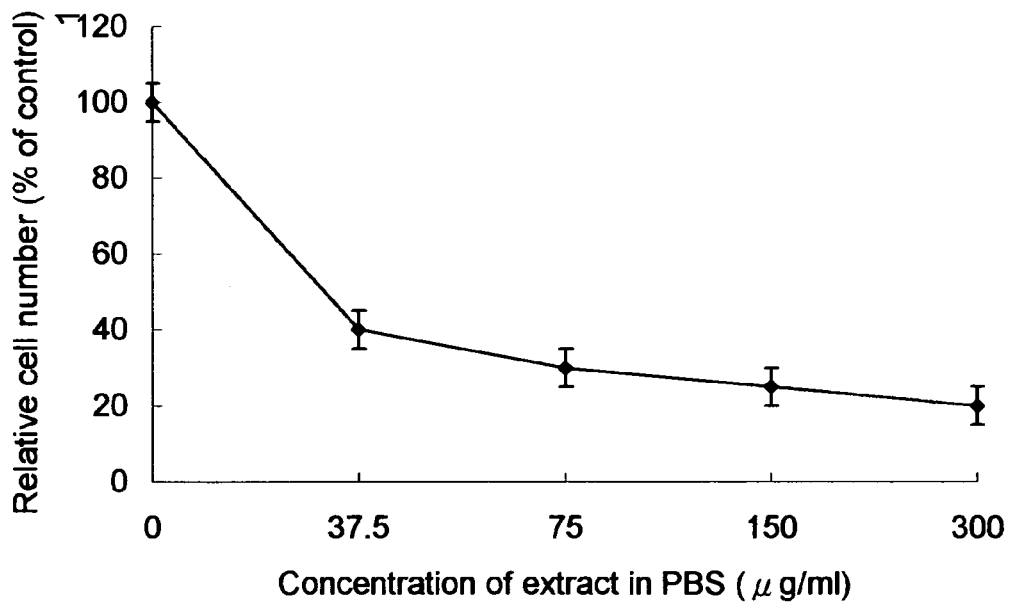
FIG. 6 shows a Hela cell proliferation assay in which the ordinate indicates relative cell number (% of control), and the abscissa indicating the concentration of extract in solution (mg/ml); $IC_{50}$: 33.5 µg/ml

The experimental procedures of Example 2 are repeated by investigating the cells of Hela to obtain data as results shown in FIG. 6.

Example 8

Figure 7:
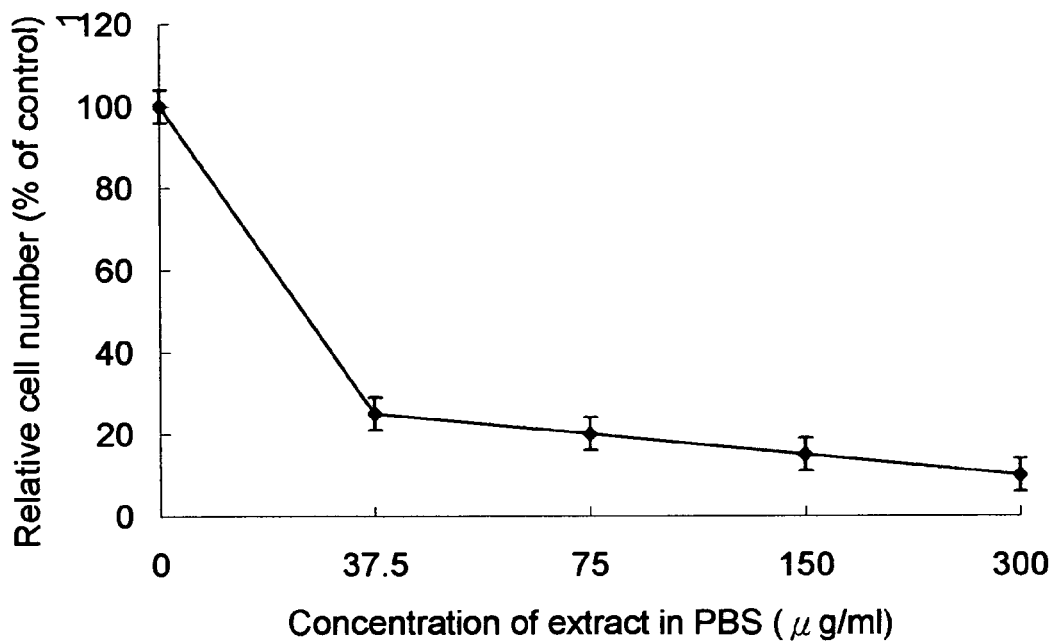
FIG. 7 shows a Paca-2 cell proliferation assay in which the ordinate indicates relative cell number (% of control), and the abscissa indicating the concentration of extract in solution (mg/ml); $IC_{50}$: 35.5 µg/ml

The experimental procedures of Example 2 are repeated by investigating the cells of Paca-2 to obtain data as results shown in FIG. 7.

Example 9

Figure 8:
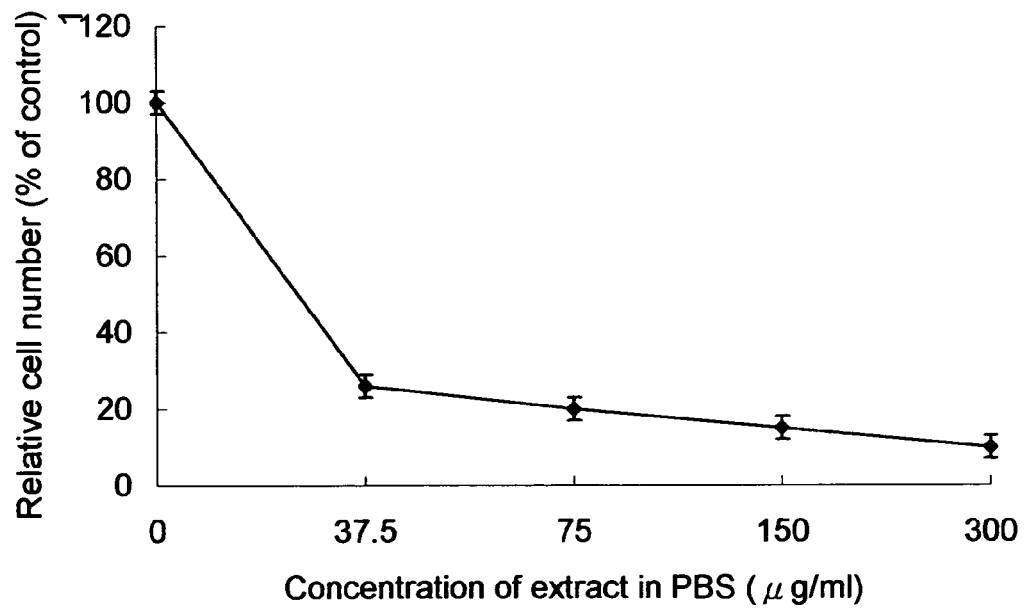
FIG. 8 shows a AGS cell proliferation assay in which the ordinate indicates relative cell number (% of control), and the abscissa indicating the concentration of extract in solution (mg/ml); $IC_{50}$: 37.0 µg/ml

The experimental procedures of Example 2 are repeated by investigating the cells of AGS to obtain data as results shown in FIG. 8.

Example 10

Figure 9:
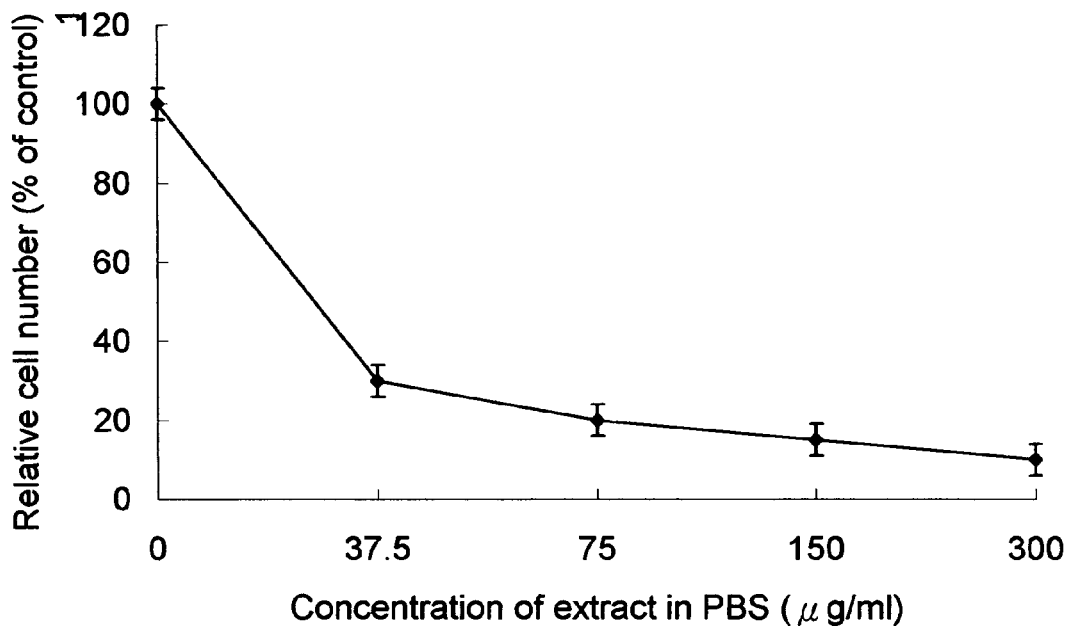
FIG. 9 shows a HepaG2 cell proliferation assay in which the ordinate indicates relative cell number (% of control), and the abscissa indicating the concentration of extract in solution (mg/ml); $IC_{50}$: 39.5 µg/ml

The experimental procedures of Example 2 are repeated by investigating the cells of HepaG2 to obtain data as results shown in FIG. 9.

Example 11

In Vivo Test of Animal Module of Suppressing Malignant Tumor

The chosen C57BL/6 mice were 20 grams in an average of weight. Then, divided into bellowed 2 groups, 10 mice (5 males, 5 females) of each group for experiment.

(c) The controlled group: Each one injected with LLC-1 for $5 \times 10^6$ cells, 7 days later, daily fed to basal diet. Daily observed till the $30^{th}$ day for anatomy.

(d) The treated group: Each one injected with LLC-1 for $5 \times 10^6$ cells, 7 days later, daily fed to 2 grams of the "extract" by weight of per kg of C57BL/6 in basal diet. Daily observed till the $30^{th}$ day for anatomy.

Figure 14:
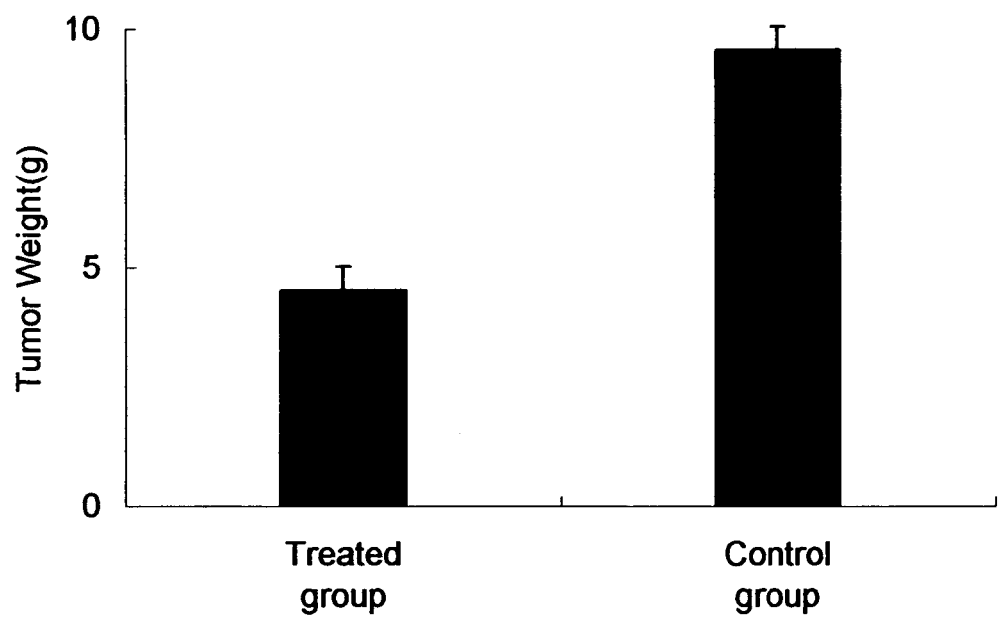
FIG. 14 shows a related weight of tumors of the treated group and of the controlled group of C57BL/6.

Removed and weighed the tumors of both groups to obtain the results: (as shown in FIG. 14)

(c) The average weight of tumor of the controlled group was 9.55±0.05 grams on the $30^{th}$ day.

(d) The average weight of tumor of the treated group was 4.52±0.05 grams on the $30^{th}$ day.

It proved the "extract" effectively suppressed the malignant tumor, cancer.

Example 12

In Vivo Test

Followed by Example 11, on the 11$^{th}$ day, bleeding 0.2 ml blood of the controlled group and of the treated group; centrifuged for serum collect, measured the level of ALT/GPT by biochemical analyzer.

Figure 11:
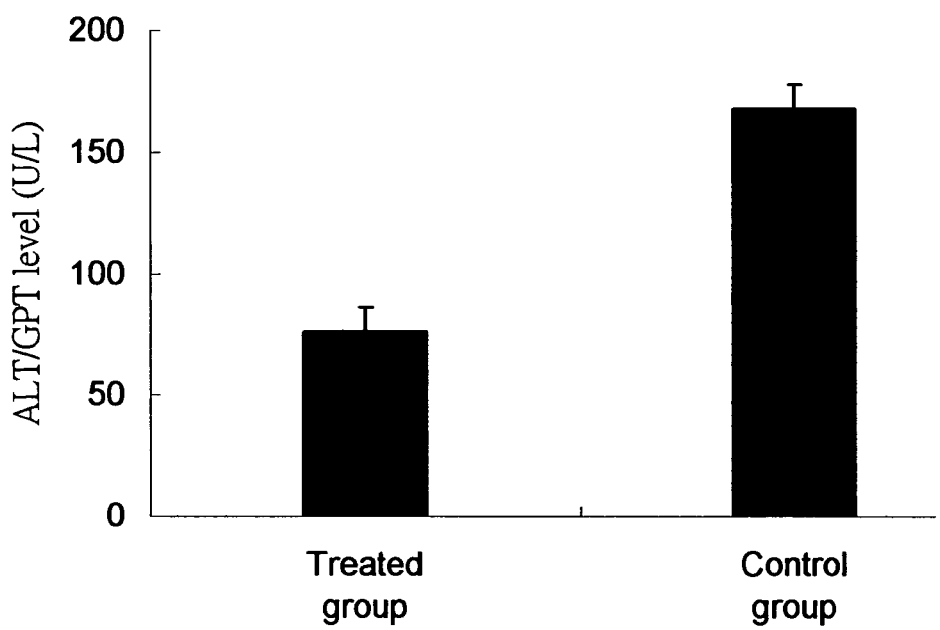
FIG. 11 shows a relationship to the concentration of Alanine Aminotransferase (ALT/GPT) of the treated group and of the controlled group of C57BL/6.

Results: (as shown in FIG. 11)

(c) The average level of ALT/GPT of the controlled group was 168 U/L.

(d) The average level of ALT/GPT of the treated group was 76 U/L.

The normal range of level should be in 28~132 U/L for a functional liver. The controlled group happened to acute hepatitis but the treated group did not. The extract suppressed acute hepatitis and played an important role in improving functions of liver.

Example 13

In Vivo Test

Followed by Example 11, on the 11$^{th}$ day, bleeding 0.2 ml blood of the controlled group and of the treated group; centrifuged for serum collect, measured the level of AST/GOT by biochemical analyzer.

Figure 10:
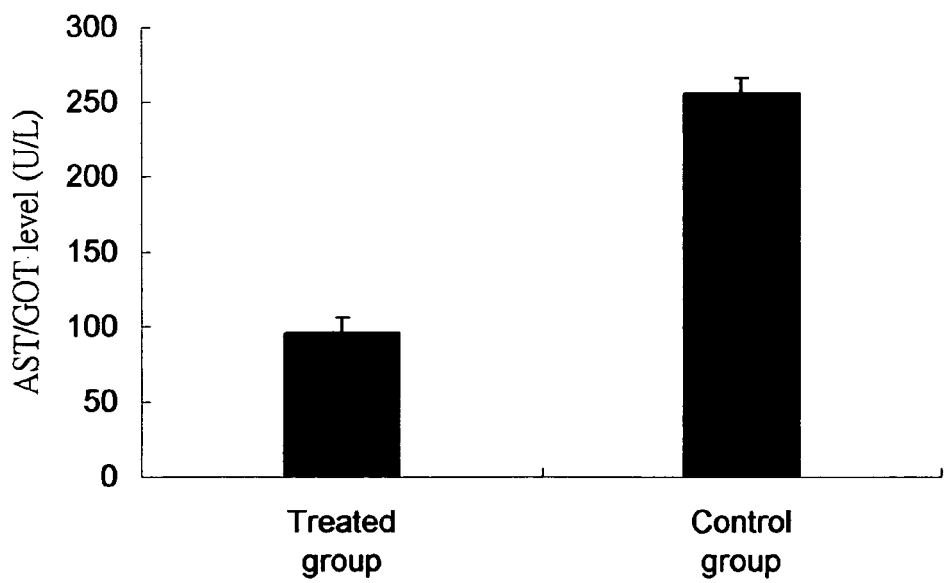
FIG. 10 shows a relationship to the concentration of Aspartate Aminotransferase (AST/GOT) of the treated group and of the controlled group of C57BL/6.

Results: (as shown in FIG. 10)

(c) The average level of AST/GOT of the controlled group was 256 U/L.

(d) The average level of AST/GOT of the treated group was 96 U/L.

The normal range of level should be in 59~247 U/L for a functional liver. The controlled group happened to chronic hepatitis but the treated group did not. The "extract" suppressed chronic hepatitis and again to play an important role in improving functions of liver.

As well known, acute hepatitis with chronic hepatitis becomes a critical condition of liver, it was also found to happen to cells death of liver of the controlled group in further pathologic examinations. The "extract" suppressed a malignant condition of hepatitis as a medical effect of hepatotherapy.

Example 14

In Vivo Test

Followed by Example 11, the numbers of platelet in plasma of the controlled group and of the treated group were counted by cell counter on the 30$^{th}$ day.

Figure 12:
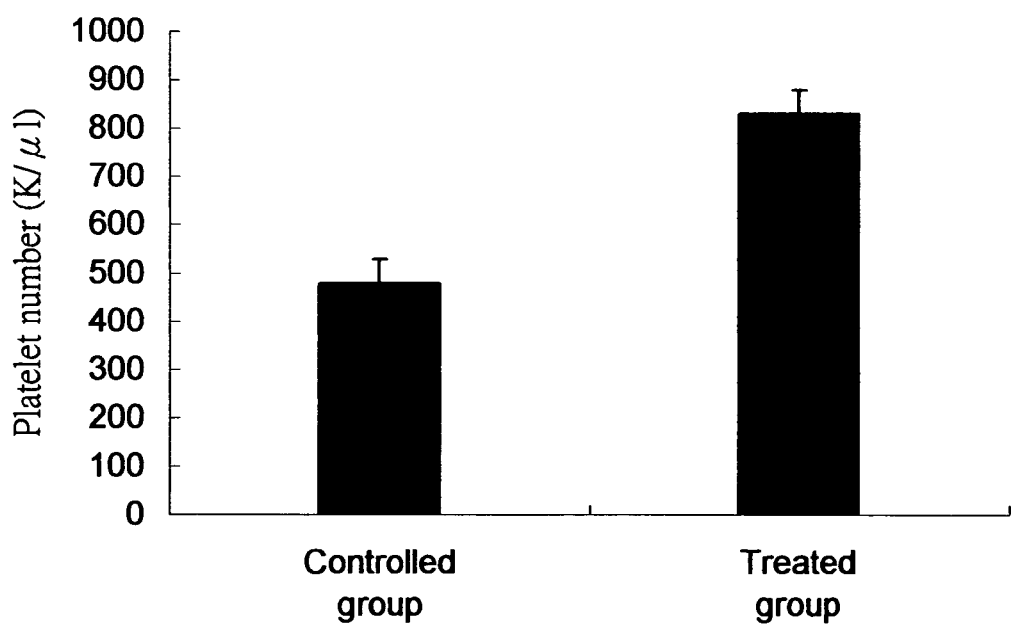
FIG. 12 shows a relationship to the numbers of platelet of the treated group and of the controlled group of C57BL/6.

Results: (as shown in FIG. 12)

(c) The average level of platelet of the controlled group was 478 k/μl.

(d) The average level of platelet of the treated group was 829 k/μl.

As well known, platelets are produced partly by liver. Deficiency of platelet failed to coagulate when bleeding. Therefore, it proved the "extract" suppressed a malignant condition of platelet disorder.

Example 15

In Vivo Test

Followed by Example 11, on the 15$^{th}$ day, bleeding 0.2 ml of blood of the controlled group and of the treated group; centrifuged for serum collect, measured the level of BUN by biochemical analyzer.

Figure 13:
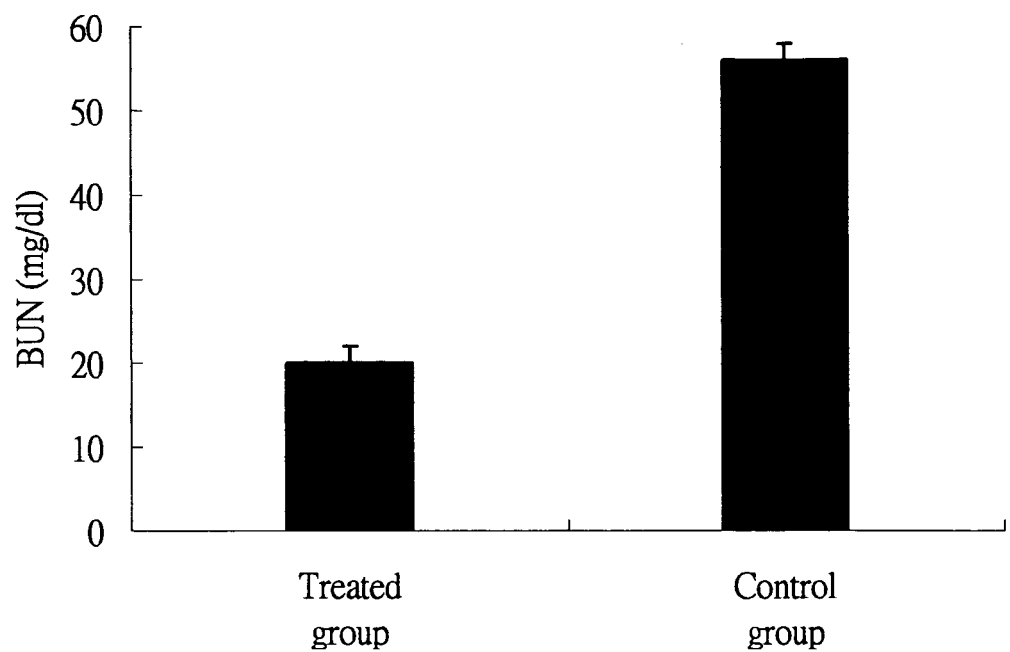
FIG. 13 shows a relationship to the concentration of Urea Nitrogen (BUN) of the treated group and of the controlled group of C57BL/6.

Results: (as shown in FIG. 13)

(c) The average level of BUN of the controlled group was 56 mg/dl.

(d) The average level of BUN of the treated group was 20 mg/dl.

The normal range of level should be in 18~29 mg/dl. Apparently, the renal function of the controlled group was damaged, but of the treated group was not. Therefore, the "extract" suppressed the renal or urinary disease, and improved functions of kidney.

Example 16

In Vivo Toxicity Test

Selected 10 rats (5 moles, 5 females) in an averaged weight of 220-250 g of each rat. 8 rats, as the test group, fed to 2 g of "extract" by weight of per kg in basal diet. The other 2 rats fed to basal diet as the controlled group. Daily fed for 28 days, observed and recorded to an average.

Results:

|  |  | WBC (k/μl) | RBC (k/μl) | Hb (g/dl) | Platelet (k/μl) | Hair&Skin | Weight (g) | Toxic Syndrome |
|---|---|---|---|---|---|---|---|---|
| The 1$^{st}$ day | Test | 4.55 | 6.6 | 12.1 | 655 | Normal | 255 | None |
|  | Controlled | 4.70 | 8.2 | 13.3 | 553 | Normal | 251 | None |
| The 28$^{th}$ day | Test | 5.35 | 7.2 | 12.5 | 672 | Normal | 571 | None |
|  | Controlled | 4.05 | 7.9 | 12.8 | 532 | Normal | 585 | None |

It proved the "extract" is non-toxic by oral administration.

It should be also be understood the foregoing relates to only a preferred embodiment of the invention and that it is intended to cover all changes and modifications of the examples of the invention herein chosen for purposed of the disclosure, which do not constitute departures from the spirit and the scope of the invention.

INDUSTRIAL APPLICABILITY

The invention is prepared for suppressing cancer, hepatitis or abnormal hepatic function, renal disorder or abnormal urinary function as well as hemopoietic disorder. Also, it is for improving functions of liver and kidney.

A preferred embodiment of composition may be optionally adjusted for a proper formulation and applied for a human being as follows:

| | |
|---|---|
| *Canavalia ensiformis* extract | 80%-98% (by weight); |
| Nutritional supplements | 3%~10% (by weight); |
| Preservatives | 0.5%~3% (by weight); |
| Buffers | 0.5%~3% (by weight); |
| Stabilizers | 1%~4% (by weight); |

Other excipients may be further added into the above composition as mentioned.

I claim:

1. A method for treating a disorder or a complication associated with cancer in a subject having cancer comprising administering an effective amount of a water-soluble *Canavalia ensiformis* extract to said subject, wherein the disorder or the complication is selected from the group consisting of hepatitis, hemopoietic disorder, platelet disorder, and renal disease and whereby the soluble *Canavalia ensiformis* extract is prepared by a process comprising grinding *Canavalia ensiformis* seeds into a crude powder, salting in a solution containing greater than 30% sodium chloride, stirring the solution for approximately 4 hours to form a first precipitate, collecting the first precipitate, dissolving the first precipitate to obtain a suspension, adding ammonium sulfate to the suspension to form a second precipitate, collecting the second precipitate, dissolving the second precipitate in water for 4 hours to obtain the water-soluble *Canavalia ensiformis* extract.

2. The method according to claim 1, wherein said composition provides for functional kidney improvement and/or functional liver improvement.

3. The method according to claim 1, wherein said water-soluble *Canavalia ensiformis* extract is administered within a nutritional supplement.

4. The method according to claim 3, wherein said nutritional supplement comprises a mineral compound selected from the group consisting of calcium, chloride, sodium, potassium, magnesium, sulfur, phosphorus, zinc, iron, copper, iodine and manganese.

5. The method according to claim 1, wherein an excipient is added to said water-soluble *Canavalia ensiformis* extract.

* * * * *